United States Patent [19]

Aebischer et al.

[11] Patent Number: 4,878,913
[45] Date of Patent: Nov. 7, 1989

[54] DEVICES FOR NEURAL SIGNAL TRANSMISSION

[75] Inventors: Patrick Aebischer; Robert F. Valentini; Pierre M. Galletti, all of Providence, R.I.

[73] Assignee: Pfizer Hospital Products Group, Inc., New York, N.Y.

[21] Appl. No.: 93,371

[22] Filed: Sep. 4, 1987

[51] Int. Cl.[4] .............................. A61F 2/04; A61F 2/72
[52] U.S. Cl. ................................ 623/12; 623/24; 623/25; 623/66
[58] Field of Search ............... 623/66, 12, 24, 25; 128/1 R, 334 R, 642; 439/70; 437/93, 188; 204/286, 28 R, 290 R

[56] References Cited

U.S. PATENT DOCUMENTS

| | | | |
|---|---|---|---|
| 3,786,817 | 1/1974 | Palma | 128/334 |
| 3,833,002 | 9/1974 | Palma | 128/334 |
| 3,916,905 | 11/1975 | Kuhn | 128/334 |
| 3,955,560 | 5/1976 | Stein et al. | 623/66 X |
| 3,960,152 | 6/1976 | Augurt et al. | 128/335 |
| 3,988,411 | 10/1976 | Capozza | 264/184 |
| 4,011,861 | 3/1977 | Enger | 623/66 X |
| 4,033,938 | 7/1977 | Augurt et al. | 260/78.3 |
| 4,074,366 | 2/1978 | Capozza | 3/1 |
| 4,369,104 | 1/1983 | Beckley | 204/286 |
| 4,461,304 | 7/1984 | Kuperstein | 128/642 |
| 4,481,353 | 11/1984 | Nyilas et al. | 528/303 |
| 4,534,349 | 8/1985 | Barrows | 128/334 |
| 4,623,355 | 11/1986 | Sawruk | 623/66 |
| 4,662,884 | 5/1987 | Stensaas | 623/66 X |

FOREIGN PATENT DOCUMENTS 0261833 3/1988 European Pat. Off. .

OTHER PUBLICATIONS

Midgley et al., *Surgical Forum*, vol. 19, pp. 519–520, 1968.
Ducker et al., *J. Neurosurg.*, vol. 28, pp. 582–587, 1967.
Molander et al., *Muscle & Nerve*, vol. 5, pp. 54–57, 1982.
Lundborg et al., *Journal of Neuropathology and Experimental Neurology*, vol. 41, No. 4, pp. 412–422, 1982.
Uzman et al., Journal of Neuroscience Research, vol. 9, pp. 325–338, 1983.
Nyilas et al., Trans Am Soc Artif Intern Organs, vol. XXIX, pp. 307–313, 1983.
Sickel et al., *Plastic & Reconstructive Surgery*, vol. 74(2), pp. 173–181, 1983.
daSilva et al., *Brain Research*, vol. 342, pp. 307–315, 1985.
Edell, *IEEE Trans.*, vol. BME-33, No. 2, (Feb. 1986).

Primary Examiner—Alan W. Cannon
Attorney, Agent, or Firm—Thomas J. Engellenner; Ann L. Kerner

[57] ABSTRACT

Devices and methods for transmitting neural signals from a proximal stump of a transected nerve to a prosthetic apparatus are disclosed employing microelectrodes, preferably conductive fiber networks, capable of sensing electrical signals from a nerve and transmitting such signals to a prosthetic apparatus; and a semipermeable guidance channel disposed about the microelectrodes. The channels include an opening adapted to receive the proximal stump of a transected nerve, such that the channel promotes the growth of the stump and the formation of an electrical connection between the transected nerve and the microelectrode.

16 Claims, 1 Drawing Sheet

DEVICES FOR NEURAL SIGNAL TRANSMISSION

BACKGROUND OF THE INVENTION

The technical field of this invention concerns medical devices useful for the transmission of neural information from transected nerves to prosthetic apparatus, and methods for preparing and using such devices for controlling prosthetic apparatus.

When a peripheral nerve is transected (or severed) as a result of surgery or trauma, axons or specialized nerve cell appendages in the distal (the furthest away from the spinal cord) portion of the severed nerve degenerate and eventually die, leaving only the sheath in which they were contained. The axons in the proximal stump which are still connected to the spinal cord or dorsal root ganglion have the ability to regenerate provided that transection has not occurred too close to the nerve cell body. Factors in the degenerating distal stump appear to exert a positive influence on regeneration, a phenomenon termed "neurotropism". The absence of a distal stump in cases of amputation seems to inhibit nerve regeneration from the proximal stump.

The development of a technology suitable for the transmission of neural information from amputated limbs to prostheses has constituted a formidable problem. Although successful interfacing of the proximal stump of transected nerves with electrode structures has been accomplished in amphibians (see Marks, "Bullfrog Nerve Regeneration Into porous Implants", Vol. 163, *Anatom. Rec.*, p. 226 (1969)), with the first recordings taken from frog nerves by Maynard et al. in "Regeneration Electrode Units...", Vol. 183, *Science*, p. 547-549 (1974), reliable recordings from mammals using similar techniques have thus far not been obtained.

The unsuccessful or unsatisfactory mammalian results to date have been related, in part, to the use of extracorporeal devices employing gross electrodes. Another cause of the poor results appears to be due to poor alignment of the cut ends of the fascicles (nerve bundles within the nerve trunk) with the implanted microelectrodes. Attempts have been made to improve the electrical connection between the nerve and the electrode by suturing the nerve to the electrode, or by provision of an indirect contact via an electrical charge-conducting gel material. A gel-impregnated silicon transducer is disclosed, for example, in U.S. Pat. No. 4,623,355 issued to Sawruk on Nov. 18, 1986. Additionally, Edell, "A Peripheral Nerve Information Transducer...", Vol. BME-33, *IEEE Transaction of Biomedical Engineering*, pp. 203-214 (1986), has reported the use of a micromachined silicon device to extract nerve signals. Nonetheless, reliable devices for extracting neural signals from the nerves of amputated limbs in mammals heretofore have not been demonstrated.

An additional impediment to successful nerve-electrode connection is the trauma produced by the manipulation of the nerve end, and the subsequent suturing typically employed to maintain alignment. The trauma appears to stimulate the growth and/or migration of fibroblasts and other scar-forming connective tissue cells which prevent the regenerating axons in the proximal stump from reaching, making intimate contact with, or maintaining contact with the electrode.

In the area of nerve repair, (i.e., the regeneration of axons from the proximal stump to a distal stump) other approaches have been taken in attempts to lessen scar-forming trauma. These have included the use of nerve cuffs and channels to position the severed nerve and guide its regeneration. For example, Ducker et al. used silastic cuffs for nerve repair in Vol. 28, *J. Neurosurg.*, pp. 582-587 (1968). Silicone rubber sheathing for nerve repair was reported by Midgley et al. in Vol. 19, *Surgical Forum*, pp. 519-528 (1968) and by Lundborg, et al. in Vol. 41, *J. Neurophathol. Expt. Neurol.*, pp. 412-422 (1982). The use of bioresorbable polyglactin mesh tubing was reported by Molander et al. in Vol. 5, *Muscle & Nerve*, pp. 54-58 (1982), and the use of semipermeable acrylic copolymer tubes in nerve regeneration was disclosed by Uzman et al. in Vol. 9, *J. Neurosci. Res.*, pp. 325-338 (1983).

However, the use of such nerve guidance materials can often add further problems. For example, some of the materials identified above have lead to inflammatory reactions in the test animals and/or have failed to exclude scar tissue formation within the channels. Moreover, the total number of axons, the number of myelinated axons, the thickness of the epineurium, and the fascicular organization of nerves regenerated within guidance channels are all typically less than satisfactory and compare poorly with the original nerve structure of the test animals.

There exists a need for better devices and methods for the transmission of neural signals from severed nerves in an amputated limb to a prosthesis. Devices and methods for the transmission of neural signals which would minimize surgical trauma, prevent interference with nerve growth by scar tissue, lessen immune responses, and improve the chances for successful regrowth of myelinated nerve and for maintenance of stable contact with the electrode would satisfy a long-felt need in this field.

SUMMARY OF THE INVENTION

It has been discovered that the proximal stump of a transected nerve can regenerate through a semipermeable guidance channel in the absence of the distal stump, and can make stable contact with an electrode disposed within that channel. Implantable devices comprising such guidance channels and electrodes disposed therein are useful for the transmission of neural signals from a severed nerve to a prosthesis. Such devices constructed Particularly of conductive fiber electrodes and tubular, semipermeable channels are disclosed for use in the transmission of neural signals from a transected nerve to a prosthesis.

In the present invention, electrodes are employed to transmit neural signals from the stump to the prosthesis. They can be constructed of any conductive material which is also biocompatible, the preferred embodiments being formed of carbon fibers, platinum fibers or the like. The electrodes of the present invention can take various shapes but are preferably mounted as a network of parallel fibers traversing the lumen of the nerve guidance channel. The number of fibers can range up to 100 individual strands or more, but preferably range from about 5 to about 25 strands. The diameter of each fiber can range from about 10 microns to about 50 microns, and the spacing between fibers can range from about 50 microns to about 500 microns. The electrodes are preferably secured to a yoke which is disposed about the outside of the nerve guidance channel and which provides a convenient location for the connection to, and insulation of, lead wires for the individual fibers.

The yoke can be disposed about the guidance channel at any distance along the length of that channel, preferably from approximately half way (3 mm) to three quarters of the way (4.5 mm) from the proximal end. It can be connected to a prosthesis or recording device via any connective means capable of transmitting electrical signals.

In another aspect of the invention, "channels" or tubular nerve guides are employed to receive the stump of a transected nerve. The tubular channel defines a lumen through which axons can be directed to regenerate in order to make contact with an electrode disposed therein. Such channels prevent, or at least retard, the infiltration of scar-forming connective tissue. Preferably the channels are formed from a porous, selectively permeable material which allows growth-promoting factors from the immediate environment to diffuse into the channel, while protecting the regenerating nerve from any inflammatory or immune responses generated due to incompatibility with the materials of which the electrode may be constructed. In addition, nerve guidance channels encourage nerve regeneration by concentrating growth-Promoting factors elicited by the stump or by retaining artificially seeded factors within the channel.

The terms "semipermeable", "permselective" and "selectively permeable" are used herein to describe materials which allow the exchange of nutrients and other metabolites with the regenerating nervous tissue while excluding fibroblasts and other scar-forming cells. For further details on semipermeable nerve guidance channels, see commonly owned U.S. patent application Ser. No. 032,489 filed Mar. 30, 1987, herein incorporated by reference. Channels according to the present invention can be formed from various semipermeable polymeric materials which allow the passage therethrough of small molecular weight molecules. The upper limit on permeability can range from about 5,000 to about 200,000 daltons. The channels of the preferred embodiment have an upper limit on permeability ranging from about 50,000 to about 150,000 daltons.

It has been determined that capping the distal end of the channel results in enhanced regeneration of the proximal stump. The regenerated nerve tissues in such capped, semipermeable channels have a histological appearance which more closely resembles normal nervous tissue than does that found in devices constructed from uncapped semipermeable, or capped or uncapped impermeable channels. (This may be due to the concentration of growth factors elicited from the regenerating nerve stump within, or of similar factors which have been elicited by other cells in the general environment of the wound, and which have diffused into the device.) Capping can be performed by occluding an opening in the channel opposite the opening adapted to receive the nerve stump. Occlusion can be accomplished with any biocompatible material. The occluding material can be the same or similar copolymer of which the channel is composed, and can be applied to the channel opening as a solution.

The nerve guidance channels of the present invention can also be constructed of semipermeable piezoelectric materials. Upon deformation, such piezoelectric materials can induce nerve growth within the lumen. The term "piezoelectric materials" as used herein is intended to encompass natural and synthetic materials capable of generating electrical charges on their surface when subjected to mechanical strain. These transient electrical charges augment the ability of axons to regenerate. Preferably, the piezoelectric materials are also semipermeable or are constructed as meshes or copolymer mixtures to provide the preferred ranges of permeability across the channel walls. For further details on piezoelectric nerve guidance channels, see commonly-owned U.S. patent application Ser. No. 025,529 filed Mar. 13, 1987, herein incorporated by reference.

The nerve guidance channels of the present invention are also preferably designed to retain nerve growth-promoting factors secreted at the anastomatic side or seeded therein, as well as to retain any luminal matrix material placed inside the guidance channels. Such factors include nerve growth factor (NGF), macrophage-derived growth factor (MDGF), platelet-derived growth factor (PDGF), fibroblast growth factor (FGF), fibronectin, laminin, and alpha-1-acid glycoprotein. The porosity of the channel material can be selected so as to control the diffusion of these factors and nutrients therethrough, while maintaining an immune barrier between the anastomatic site and the patient's immune system.

It has also been discovered that particular structural configurations of the guidance channel can play an important role in optimizing nerve regrowth conditions. Semipermeable, tubular channels which have a smooth, inner surface result in significantly larger regenerated nerve cables and higher numbers of regenerated myelinated axons. In one preferred embodiment, the guidance channels of the present invention comprise tubular membranes featuring relatively large (i.e., on the order of about 1 to about 20 microns) pores on the outside, intercommunicating voids in the membrane, itself, and a smooth inner skin having relatively small (i.e., on the order of about 100 to about 800 angstroms) pores.

The relatively large outside pores and the intercommunicating voids permit capillary ingrowth into the wall of the synthetic tube which allows more optimal metabolic support, while the relatively small pores of the inner membrane prevent the invasion of scar-forming cells within the regenerating environment. Additionally, it is preferable to employ devices having membranes with longitudinally oriented trabeculae rather than radially oriented trabeculae. Studies to date reveal that longitudinally oriented trabeculae can support a larger number of capillaries and yield nerve cables with larger numbers of axons.

Preferably, the membrane wall thickness of the semipermeable nerve guidance channels of the present invention will range from about 0.05 to about 1.0 millimeters depending upon the particular electrode and membrane material employed, and on the application. Similarly, the diameter of the lumen can vary from about 0.5 millimeters to about 2 centimeters, depending upon the size of nerve to be connected to the electrode network.

The transmission device of the present invention can be used by locating the severed proximal nerve stump, and selecting an appropriately sized electrode and semipermeable guidance channel for interfacing with a prosthesis. The channel of the present device comprises an opening adapted to receive the severed nerve stump, and a lumen to permit regeneration of the nerve therethrough to contact the electrode disposed therein. The nerve stump is then gently drawn into tube by manual manipulation or suction, placed in optimal proximity, and then secured in position without undue trauma by sutures, a biocompatible adhesive (e.g., fibrin glue), or by frictional engagement with the tube. Antibiotics can be administered to the site, and the wound is then closed.

The term "nerve" is used herein to mean both monofascicular and polyfascicular nerves. The same general principles of regeneration are applicable to both.

The invention will next be described in connection with certain preferred embodiments; however, it should be clear that the invention may be embodied in other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

For example, although the illustrated device for transmission of neural signals comprises a disc-shaped yoke with carbon-based fiber electrodes, electrodes having a different shape or composed of other biocompatible materials capable o conducting electrical signals may be employed instead. Multiple networks of conductive fibers (e.g., orthogonal or otherwise offset at an angle to each other) can also be employed. The semipermeable nerve guidance channel in which the electrode is placed, and which is described below as being generally tubular in shape, can also have various alternative shapes, as can its lumen. The material from which the channel is made can be permeable to molecules of varying molecular weights. Moreover, sheet materials can be employed and formed into nerve guidance tubes in situ. In such a procedure, the nerve stump and electrode can be placed on top of the sheet and secured thereto by sutures, adhesives or friction. The sheet can then be wrapped around the nerve segment and the resulting tube closed by further sutures, adhesives or friction. The guidance channel also can be constructed from two or more parts which are clamped together to secure the nerve stumps. It can further comprise one or any number of growth-factors. In addition, other materials can also be used to fill the luminal cavity of the device besides growth-inducing factors such as physiological saline, collagen, glycosaminoglycans, or cultured Schwann cells.

DETAILED DESCRIPTION

Figure 1:
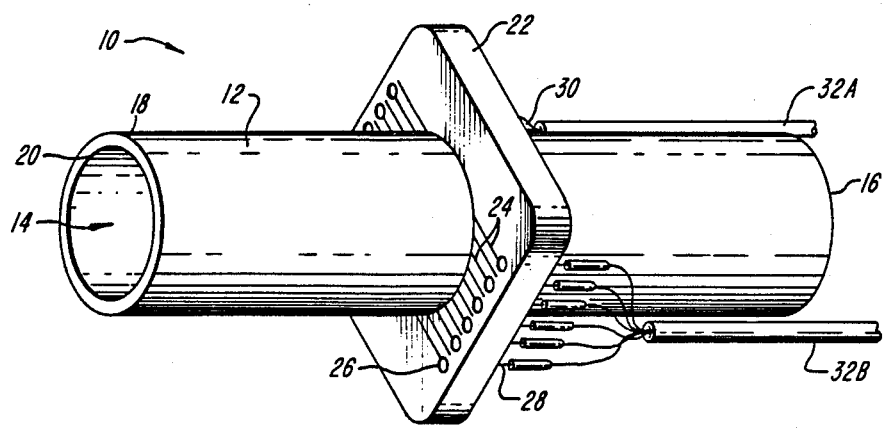
FIG. 1 is a perspective view of a device for the transmission of neural signal according to the present invention.

In FIG. 1, an apparatus 10 for neural signal transmission is shown, including a tubular nerve guidance channel 12 having an open proximal end 14 and a distal end 16 which can also be open but preferably is capped. The outer surface 18 of the nerve guidance channel 12 is preferably partially fenestrated with relatively large (e.g., 1-20 micron) pores while the inner surface 20 of the channel 12 possesses a relatively smooth skin having relatively small (e.g., 100-800 angstrom) pores. The inner and outer pores are joined by interconnected passageways to provide a supporting structure for the semipermeable inner skin of the membrane.

The nerve guidance channel 12 can be formed, for example, from an acrylic copolymer. Tubular membranes of this type can be obtained, for example, from the Amicon Corporation of Lexington, MA (XM50 tubing, a polyvinyl chloride acrylic copolymer, molecular weight cutoff approximately 50,000 having an internal diameter of about 1 millimeter and a wall thickness of about 100 $\mu$m). The distal end 16 can be sealed by dipping it into an epoxy glue or a polymeric solution of the same composition as the membrane.

The apparatus 10 of FIG. 1 also includes an electrode yoke 22 disposed about the channel 12 and a plurality of electrodes 24, preferably constructed from carbon fibers and mounted onto connectors 26 on the yoke 22. The connectors 26 provide individual connections to posts 28, which are adapted to receive lead wires 30 from electrode wire bundles 32A, 32B. The yoke 22 is preferably constructed of silicon or other insulating biocompatible material. Lead wires 30 and bundles 32 are similarly coated with a biocompatible polymeric material, such as silicone, polytetrafluoroethylene or polyurethane.

Figure 2:
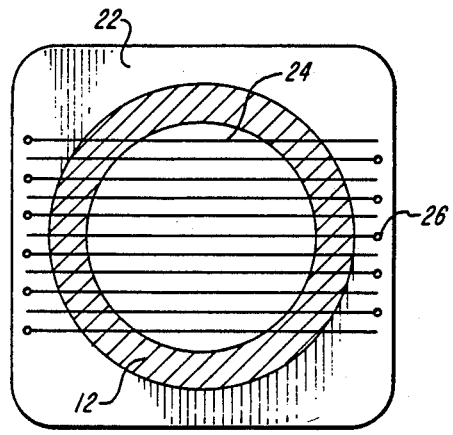
FIG. 2 is a cross-sectional view of the electrode yoke and fiber electrodes of the device of FIG. 1. pg,2

As shown in more detail in FIG. 2, electrodes 24 pass through the tubular membrane of channel 12 and form a network of parallel strands within the lumen of the channel. The diameter of the individual fibers 24 can range from about 10 microns to about 50 microns and the spacing between fibers can range from about 50 microns to about 500 microns depending on the size of the lumen and the nerve.

In use, the proximal end of a severed nerve is drawn into the tubular channel 12 and allowed to grow by regenerative processes into the channel until it makes electrical contact with electrode network 24. Electrical signals from the nerve can then be transmitted via the electrodes 24 and lead wires 32 to a prosthetic device. The prosthetic device (not shown) can further include low noise amplifiers, filters and threshold trigger circuits, as known in the art of signal processing, to extract the neural motor signals necessary to control the prosthetic device.

To further demonstrate the usefulness of the present invention in inducing the growth of a proximal nerve stump even in the absence of a distal stump, an experiment was conducted on young albino mice. The mice (Sprague Dawby, 25-30 grams) were anesthetized by inhalation of methoxyflurane. The left sciatic nerve was exposed through a skin incision along the anterior medial aspect of the thigh after retracting the gluteus maximus muscle. The nerve was transected about 8 mm proximal to the tibio-peroneal bifurcation and the remaining distal nerve branches were resected. The proximal stump was then secured 1 mm from the end of a 6 mm acrylic copolymer tube (Amicon Corp. Lexington, MA) with a single 10-0 nylon suture.

The mice were divided into two groups; in one group the proximal stumps were secured to polymer tubes with their distal ends left open, and in the other group the nerve stumps were secured to identical polymer tubes in which the distal ends were capped. In the experiments where the distal end was capped, a solution of the same acrylic copolymer was applied to the distal end to occlude it. The polymeric solution fused the tube's end and created a seal impervious to water. In all cases, the channels were primed with sterile physiological saline prior to implantation.

At retrieval time (4 or 8 weeks post procedure), the mice were again deeply anesthetized and then sacrificed by transcardial perfusion with phosphate-buffered saline followed by saline solutions of paraformaldehyde and glutaraldehyde. The operative site was reopened and the guidance channel and 3 mm of native proximal nerve were removed. Serial transverse sections of the channels and regenerated nerves were cut, fixed and stained for light microscopy and transmission electron microscopy.

All capped permselective acrylic copolymer channels contained regenerated nerve cables which extended fully to the distal end of the channel. The cables were centrally located and surrounded by an acellular gel although, in one case, the cable was in direct contact with the inner wall of the guidance channel for about 2 millimeters. The proximal nerve stump displayed the typical enlargement associated with peripheral nerve entubulation. The cross-sectional area of the cables decreased gradually as the cables extended from the original proximal nerve stump to the distal cap with a slight increase as they reached the cap end.

The regenerated nerves in the capped channels were sheathed by an epineurium-like tissue and contained numerous small blood vessels. They contained numerous myelinated axons up the to channel end, although their number decreased as they approached the distal cap. The cable did not present the typical microfasciculation normally observed in nerves regenerated through synthetic guidance channels. There was a significant increase in the number of myelinated axons between 4 and 8 weeks at each distal interval. The axons were associated with Schwann cells, which were identified from their morphological characteristics and their association with axons.

One of 3 uncapped channels at 4 weeks and 2 of 3 at 8 weeks exhibited regenerated cables extending from the proximal stump to the distal channel end. The remaining channels contained cables which extended for only 2-3 mm into the channel. Cables regenerated in uncapped channels were surrounded by an epineurium-like tissue and contained several small blood vessels. The cable cross-sectional area was significantly smaller than that of the capped ones. The cables in the uncapped channels also contained significantly fewer myelinated axons than cables in the capped acrylic copolymer channels at both time periods. Myelinated and unmyelinated axons were located in microfascicles surrounded by perineurial-like cells.

A comparative example was carried out using non-permeable silicone elastomer channels. In contrast to capped acrylic copolymer channels, capped silicone elastomer channels contained only fine threads of connective tissue which extended for no more than 1 mm from the proximal nerve stump. The cables were composed of granulation tissue with circumferentially arranged cells and did not contain any myelinated axons. The proximal native nerve stump exhibited an abnormally thick epineurium. One of 3 uncapped silicone elastomer channel at 4 weeks and 2 of 3 at 8 weeks showed small tissue cables extending up to the distal end. The cables contained numerous blood vessels and were surrounded by a relatively thick epineurium. At both time periods these structures contained fewer than 100 myelinated axons at the midpoint of the guidance channel and no myelinated axons at their distal end. Patterns of microfasciculation were observed.

Thus, the experiments demonstrate that when the proximal stump of a mouse sciatic nerve is placed into a blind-ended, 6 mm long permselective channel, a large regenerated nerve cable containing myelinated and unmyelinated axons extended to the distal end of the channel. In contrast, blind-ended silicone channels contained only fine threads of connective tissue extending for less than 1 mm from the proximal stump. Capped, permselective channels show substantial regeneration into a synthetic guidance channel in the absence of a distal nerve stump, refuting the dogma that the distal nerve stump is necessary for supporting more than just abortive sprouting from the proximal nerve stump. Growth and/or trophic factors other than those released by the distal nerve stump appear able to elicit the regeneration process.

Permselective materials appear to offer the advantages of providing a large surface area for diffusive interactions while controlling the size of the solutes which pass across the wall, and preventing any cellular invasion from the outside. Permselective channels appear to support regeneration in the absence of a distal nerve stump by allowing the inward passage of nutrients and growth or trophic factors from the external wound environment while preventing the inward passage of scar forming cells. Cells participating in the wound healing phenomena are known to release various peptide growth factors which are effective at monogram concentrations. Several of these factors have been purified and show molecular weights in the range of 20,000-40,000 daltons, thus they will pass through the wall of the acrylic copolymer channels used in this study.

Activated macrophages secrete numerous growth factors, including platelet derived growth factor (PDGF) and macrophage derived growth factor (MDGF). PDGF, for example, shows a mitogenic activity on glial cells. Macrophages are consistently observed within the trabecular structure of the acrylic copolymer guidance channels. These macrophages may be secreting growth or trophic factors into the regenerating environment. Growth factors may also be released by other cells of the wound healing process, such as endothelial cells, e.g., endothelial derived growth factor (EDGF), and fibroblasts e.g., fibroblast growth factor (FGF).

The use of a permselective channel may also allow the retention within the regenerating environment of growth or trophic factors secreted by the proximal stump. Schwann cells have been shown to secrete laminin, a high molecular weight glycoprotein, which exerts neurite promoting activity in vitro. In addition, the blood vessels located in the proximal nerve stump may supply high molecular weight serum molecules such as fibronectin or alpha-1-acid-glycoprotein, which have been shown to support neural survival and promote neurite elongation in vitro.

The greater degree of regeneration observed in capped channels compared to uncapped ones may be related to a greater retention of growth and/or trophic factors which diffused inward from the extra-channel fluid as well as the retention of growth and/or trophic factors secreted by the proximal stump.

The implications of these experiments for prosthetic interfaces are twofold: First, semipermeable channels are preferred in providing a nerve guidance path from the proximal stump to the microelectrode network. Secondly and unexpectedly, in the absence of a distal nerve stump, capped channels are also preferable to induce nerve growth and differentiation in a manner that will optimize electrical conducts between individual axons and individual electrode elements.

We claim:

1. A device for transmitting neural signals from a proximal stump of a transected nerve to a prosthetic apparatus, said transmission device comprising:
   a microelectrode capable of sensing electrical signals from a nerve and transmitting said signals to said prosthetic apparatus; and
   a guidance channel disposed about said microelectrode, comprising a tubular, semipermeable membrane and having a capped distal end and a proximal end which defines an opening adapted to receive a proximal stump of a transected nerve, whereby said channel promotes the growth of said stump, such that an electrical connection between said transected nerve and said microelectrode can be obtained.

2. The transmission device of claim 1 wherein said microelectrode comprises a conductive fiber network.

3. The transmission device of claim 2 wherein the conductive fiber network further includes an array of parallel carbon fibers which traverse the nerve guidance channel.

4. The transmission device of claim 3 wherein the carbon fibers range from about 10 microns to about 50 microns in diameter.

5. The transmission device of claim 3 wherein the spacing between carbon fibers ranges from about 50 microns to about 500 microns.

6. The transmission device of claim 2 wherein the conductive fibers are platinum fibers.

7. The transmission device of claim 2 wherein said conductive fiber network is mounted upon a yoke disposed about the channel.

8. The transmission device of claim 7 wherein the yoke comprises an insulating biocompatible material.

9. The transmission device of claim 7 wherein the yoke comprises a silicon material.

10. The transmission device of claim 1 wherein said tubular membrane further includes a lumen ranging from about 0.5 millimeters to about 2.0 centimeters in diameter.

11. The transmission device of claim 1 wherein said semipermeable channel has an upper limit on permeability ranging from about 5,000 to about 200,000 daltons in molecular weight.

12. The transmission device of claim 1 wherein said semipermeable channel has an upper limit on permeability ranging from about 50,000 to about 150,000 daltons in molecular weight.

13. The transmission device of claim 1 wherein the device further includes at least one neurotropic material seeded within the channel.

14. The transmission device of claim 13 wherein the neurotropic material is selected from the group consisting of NGF, MDGF, PDGF, EDGF, FGF, laminin, fibronectin, and alpha 1-acid glycoprotein.

15. The transmission device of claim 1 wherein the channel further comprises an acrylic copolymer material.

16. The transmission device of claim 1 wherein the guidance channel further comprises a porous outer membrane surface which permits capillary ingrowth, and a smooth inner membrane surface which permits regeneration of the nerve therethrough.

* * * * *